United States Patent [19]

Nosowitz

[11] Patent Number: 4,895,977
[45] Date of Patent: Jan. 23, 1990

[54] PURIFICATION OF ALKANESULFONIC ACIDS USING OZONE

[75] Inventor: Martin Nosowitz, Easttown, Pa.

[73] Assignee: Pennwalt Corporation, Philadelphia, Pa.

[21] Appl. No.: 283,112

[22] Filed: Dec. 12, 1988

[51] Int. Cl.$^4$ .......................................... C07C 139/00
[52] U.S. Cl. ................................... 562/124; 562/118; 562/35; 562/36; 562/37; 562/104; 562/108; 562/109
[58] Field of Search ................... 260/513 R; 562/124, 562/118, 35, 36, 37, 104, 108, 109

[56] References Cited

U.S. PATENT DOCUMENTS

| | | | |
|---|---|---|---|
| 2,667,507 | 1/1954 | Jones et al. | 260/513 R |
| 2,842,588 | 7/1958 | Honeycutt | 260/504 |
| 3,147,303 | 9/1964 | Krefeld et al. | 260/543 |
| 3,232,975 | 2/1966 | Merkel | 260/456 |
| 3,248,423 | 4/1966 | Stratton | 260/543 |
| 3,413,337 | 11/1968 | Bost | 260/513 |
| 3,479,398 | 11/1969 | Bost et al. | 260/513 |
| 3,485,870 | 12/1969 | Bost | 260/513 |
| 4,549,993 | 10/1985 | McElligott, Jr. | 260/543 R |

FOREIGN PATENT DOCUMENTS 2504235 8/1976 Fed. Rep. of Germany ... 260/513 R

OTHER PUBLICATIONS

J. Che. Soc. 4547–4555 (1957) "Barnard: Oxidation of Organic Sulphides".
PB-257 891, Aug. 1976, "Reaction Kinetics of Ozone with Sulfur Compounds", Montana Univ., Missoula, Dept. of Chemistry.

*Primary Examiner*—Alan Siegel

[57] ABSTRACT

The removal of oxidizable organic impurities which include alkylthiolsulfonate from alkanesulfonic acids by treatment with an ozone containing gas is disclosed. The treated products have improved color and odor and exhibit improved long-term color stability.

9 Claims, No Drawings

PURIFICATION OF ALKANESULFONIC ACIDS USING OZONE

BACKGROUND OF THE INVENTION

In the large scale production of alkanesulfonic acids by oxidation of mercaptans or dialkyl disulfides, it is desirable but extremely difficult to achieve complete oxidation of the odorous organosulfur impurities without oxidation of the product acid. Such overoxidation can result in the formation of undesired sulfate, whereas underoxidation allows small amounts of the undesirable odorous oxidizable sulfur compounds to remain. Such compounds include the starting mercaptans (RSH) and dialkyl disulfides (RSSR') as well as alkyl alkanethiolsulfonates (RSO$_2$SR'), alkyl alkanethiolsulfinates (RS(O)SR') and dialkyl sulfoxides (RSOR'), where R and R' are alkyl groups and R and R' can be the same or different. These and other impurities may cause significant unpleasant odor and lead to the formation of color. Further odor or color may develop when the alkanesulfonic acid or its aqueous solution is subsequently used as a reactant or solvent.

A number of methods of purifying sulfonic acids and their salts are known which involve treatment with various chemicals including nitric acid, cyanuric acid, sodium hypochlorite, hypobromate and hydrogen peroxide. These methods have the disadvantage of introducing new impurities into the sulfonic acid. These impurities must be removed, in some cases, such as when nitric acid is used, with great difficulty.

Honeycutt discloses the improvement of the color and wetting properties of sulfonic acid salts through contact with ozone, which has the advantage of not introducing a new impurity to the mixture being treated. The salts treated by Honeycutt are contained in petroleum sulfonate stocks derived from the sulfonation of petroleum. The color causing materials in such stocks would be expected to differ from the organosulfur impurities resuling from the formation of alkane sulfonic acids by the oxidation of mercaptans and disulfides.

Ozone has been disclosed as an initiator for the sulfoxidation of saturated hydrocarbons by Bost et al in U.S. Pat. Nos. 3,413,337, 3,479,398 and 3,485,870 to permit the use of lower reaction temperatures (below 50° C.) during the sulfoxidation process using a metal, halogen oxide, halogen oxy acid or nitrogen oxide catalyst. Thie process produces sulfuric acid as a side reaction. Ozone is reported to effect some decolorizing of the product sulfonic acids. The nature of the color causing materials is not disclosed but the byproduct sulfuric acid itself is known to cause color by the oxidation or charring of other impurities. As in the case of the Honeycutt process, such color producing compounds would be expected to differ from the organosulfur impurities derived from the oxidation of mercaptans and disulfides.

Two research papers discuss the ozonation or organic sulfides. Barnard [J. Chem. Soc., 4547–4555 (1957)] discloses the oxidation of organic mono-, di- and tetra-sulfides with ozone. Barnard reported that dimethyl disulfide was converted to methyl methanethiolsulphonate under his reaction conditions (−25° C.), rather than to the methanesulphonic acid anhydride, because the methanethiol-sulfonate did not further react with ozone. Ericson and Yates (PB-257891 August 1976) in their report of studies on the reaction kinetics of ozone with sulfur compounds disclose that ozone treatment of methanethiol at low concentrations at 0° C. produced methanesulfonic acid along with dimethyldisulfide, methyl methanethiolsulfonate and methyl methanethiolsulphinate as minor constituents and that continued ozonation resulted in very slow formation of sulfuric acid by oxidation of the acid. The above organic side products were not detected when excess ozone was present but any minor products may escape detection due to the low concentrations. Ericson and Yates indicate that with excess ozone the disulfide and thiolsulphinate would have been oxidized but they refer to Barnard's report that thiolsulfonates are resistant to ozonation.

In the large scale production of methanesulfonic acid by catalytic oxidation of methylmercaptan (methanethiol) or dimethyl disulfide, methyl methanethiosulfonate is a significant impurity which must be reduced in concentration or completely removed. Based on the above reports one would expect that ozonation would either fail to oxidize this impurity or, if more rigorous conditions were used in order to attempt to oxidize the thiolsulfonate, at the sulfonic acid product concentrations needed for a practical purification process oxidation of some of the product acid to sulfuric acid would be expected to occur. Surprisingly, I have found that the thiolsulfonate content of alkanesulfonic acids can be significantly reduced (along with other organosulfur impurities) by treatment with ozone, at temperatures of 20° C. and above and sulfonic acid concentrations of 10% or more without significant conversion of sulfonic acid to sulfuric acid.

BRIEF SUMMARY OF THE INVENTION

This invention provides a process for removing oxidizable organic impurities, which include an alkylthiolsulfonate, from an alkanesulfonic acid comprising contacting said alkanesulfonic acid with an ozone-containing gas at a temperature of from about 20° C. to 100° C.

DETAILED DESCRIPTION

The alkanesulfonic acids which may be treated by the process of the invention are those having the general formula:

$$RSO_3H$$

wherein R is an alkyl group of from one to about twenty carbon atoms.

The treatment of the sulfonic acid may be performed in the substantial absence of any solvent or it may be performed in the presence of aqueous or non-aqueous solvents. Thus, the concentration of sulfonic acid in any solvent present during treatment may be about 10% by weight or greater. While lower concentrations may be used, for most purposes such a large proportion of solvent provides no practical benefit. Suitable inert organic (non-aqueous) solvents which may be employed will be obvious to one of skill in the art. For purposes of illustration, but without limiting the generality of the foregoing, the non-aqueous solvents may include low-boiling, straight chain hydrocarbons such as n-pentane and n-octane, aromatic hydrocarbons such as benzene and toluene, and halogenated hydrocargons particularly perfluorinated straight chain hydrocarbons and mixtures of such solvents. Sulfonic acids obtained in and intended to be used in aqueous solution may be treated in such solution. It is preferred for substantially anhydrous sulfonic acids which are liquid in the preferred temperature range of treatment that they be treated as the neat liquid. If a sulfonic acid is a solid in the preferred temperature range of treatment, it is convenient that such sulfonic acid be treated in solution after being dissolved in an inert, organic solvent to provide acid concentrations by weight of from about 10% to saturation.

The method of this invention may be employed to remove colored or odorous impurities, or both. The method is made effective to remove from alkanesulfonic acids various impurities including alkanethiols of the general formula RSH, dialkyl disulfides of the general formula RSSR', dialkyl sulfides of the general formula RSR', dialkyl sulfoxides of the general formula RSOR', alkyl alkanethiolsulfinates of the general formula RS(O)SR', and alkyl alkanethiolsulfonates of the general formula $RSO_2SR'$ where R and R' are alkyl groups and can be the same or different, by selecting the appropriate conditions of temperature and treatment time.

The method of the invention when employed to treat the alkanesulfonic acids contemplated by the present invention has surprisingly been found to increase their long term color stability.

The method of this invention may be used at temperatures from about 20° to 100° Centigrade. The preferred treatment temperature is from 30° to about 80° Centigrade. Higher temperatures will increase the rate of oxidation but may promote the undesirable formation of sulfate. The treatment time is selected to provide the desired product purity and can be determined by continuous or frequent monitoring of color or impurity concentration. In general, the treatment time required may be from about 10 minutes up to 8 hours. Treatment times of more than 8 hours at elevated temperatures may result in the formation of sulfate and times of 4 hours or less are preferred.

Ozone concentrations of from about 0.001% to at least 10% by weight in oxygen, air, or another inert carrier gas such as $N_2$ or He are suitable for use in the method of the invention although higher concentrations can be used. The preferred ozone concentration will depend on the concentration of impurities present in the alkanesulfonic acid, the temperature, and the desired time for treatment. The preferred ozone concentration is from about 0.05% to 4.0% by weight. The ozone can be generated in air or oxygen by various methods known to those skilled in the art.

The process of the invention may be carried out either batchwise or in a continuous fashion and can be performed with or without agitation. Mechanical agitation of the liquid acid or water or inert organic solvent solutions is preferred. The mechanical agitation can be by stirring or forced circulation of the liquid alkanesulfonic acid or alkanesulfonic acid solution. The ozone-containing gas may be vented after a single pass through the alkanesulfonic acid solution or it may be recycled to the ozone generator.

As used herein and in the appended claims, the term alkyl group of from 1 to about 20 carbon atoms means a straight, branched chain or cyclic alkyl group which may be unsubstituted or substituted with one or more other atoms or functional groups. Such substitutes may include, but are not limited to, halogen (fluorine, chlorine, bromine, iodine), hydroxyl, alkoxy, nitro, phosphoro, alkanoyloxy, and sulfonic acid. Cyclic alkyl groups may, of course, also be substituted with substituted or unsubstituted straight or branched chain alkyl groups in addition to being unsubstituted or being substituted with one or more of the other mentioned substituents.

The process of the present invention is further illustrated by the following examples.

The treatment apparatus consisted of a glass vessel filled with 50 ml of the sample immersed in a thermostatted temperature bath. A fritted glass sparging tube was inserted into the vessel and gas sparged through the liquid. No other mixing was provided. Color was determined by optical measurements made by a spectrophotometer at 450 nm. which were correlated to the APHA color (ASTM D-1209-84). The APHA color scale is based on the concentration of a platinum-cobalt complex in aqueous solution which imparts a yellow color to the solution. The APHA scale has a range of values from 0 to 500, 0 corresponding to pure water (no discernible color) and 500 to a dark yellow solution containing 500 ppm of the platinum-cobalt complex. Since the spectrophotometer is capable of making accurate measurements above the highest APHA color number, an extrapolation was performed to allow APHA colors above 500 to be measured.

EXAMPLE 1

A 50 ml sample of darkly colored (yellow) 70% by weight aqueous methanesulfonic acid (APHA 160) was treated for 170 minutes with 0.10% by weight ozone in air at a total flow of 230 ml/min at 24° C. with the apparatus described above. The resulting solutions had an APHA color of 10, and a water-white appearance.

EXAMPLE 2

An odorous solution of 70% by weight aqueous methanesulfonic acid containing 1000 ppm of methyl methanethiolsulfonate and 1000 ppm of dimethyl disulfide was treated with 0.10% by weight ozone in air at a total flow of 230 ml/min at 60° C. in the apparatus described above. The concentration of methyl methanethiolsulfonate and dimethyl disulfide were measured by gas chromatography. After two hours, less than 1 ppm dimethyl disulfide and about 750 ppm methyl methanethiolsulfonate remained. The odor had been reduced significantly. Becuase ozone is known to oxidize dimethyl disulfide to methyl methanethiolsulfonate, the process removed an equivalent of more than 1000 ppm of methane thiolsulfonate.

EXAMPLE 3

A 740 gram sample of dark brown anhydrous methanesulfonic acid with APHA color 620 was charged to a 1000 ml flask and kept in a thermostatted bath at 60° C. Air containing 0.12% by weight ozone was bubbled through the sulfonic acid at a rate of 230 ml/min, and overhead gas was recycled at a rate of 1500 ml/min. The sulfonic acid was removed from the flask by a pump at the rate of 95 ml/min and returned to the flask. Stirring was effected by a magnetic stiring bar. The color of the sulfonic acid was continuously monitored by spectrophotometer and after 24 minutes had decreased to about APHA 20 and appeared water-white.

EXAMPLE 4

A 50 ml sample of an odorous solution of 70% by weight aqueous methanesulfonic acid containing 500 ppm of methyl methanethiolsulfonate and 484 ppm sulfate was treated with 0.10% by weight ozone in air at a total flow of 230 ml/min at 80° C. in the apparatus used for Examples 1 and 2. The concentration of methyl methanethiolsulfonate was measured by gas chromatography, and that of sulfate by ion chromatography. After 4 hours of the treatment, 76 ppm methyl methanethiolsulfonate and 531 ppm sulfate were found and the odor had been reduced greatly. A second 50 ml sample of the same material treated for the same length of time at the same temperature with air rather than ozone was found to contain 490 ppm methyl methanethiolsulfonate and 471 ppm sulfate after treatment and maintained its odor.

EXAMPLE 5

A 50 ml sample of dark brown (APHA about 320) anhydrous methanesulfonic acid was treated for 60 minutes with 0.10% by weight ozone in air at a total flow of 230 ml/min at 60° C. in the apparatus used for Examples 1 and 2. The resulting solution had an APHA color of about 20 and a water-white appearance. When analyzed by Ion Chromatography, the starting material was found to contain 309 ppm sulfate and the ozone-treated material was found to contain 343 ppm sulfate. Since the two measurements are within the reproducibility limits of the instrument, about 10 percent, no significant increase in sulfate concentration was detected.

The present invention may be embodied in other specific forms without departing from the spirit of the invention, and the foregoing examples are not intended to limit the scope of the invention.

I claim:

1. A process for removing oxidizable organic impurities, which include an alkyl alkanethiolsulfonate, from an alkanesulfonic acid comprising contacting said alkanesulfonic acid with an ozone-containing gas at a temperature of from about 20° C. to 100° C.

2. The process of claim 1 wherein said ozone-containing gas has an ozone concentration in the range of from about 0.001 to 10% by weight.

3. The process of claim 2 wherein said alkanesulfonic acid is contacted with said ozone-containing gas for from about 10 minutes to 8 hours.

4. The process of claim 1 wherein said alkanesulfonic acid has the general formula $RSO_3H$ where R represents an alkyl group having 1 to 20 carbons contained in a straight or branched chain or in a cycloalkyl group having 3 to 6 carbon atoms in the ring.

5. The process of claim 4 wherein R is substituted by halogen, hydroxyl, lower alkyl ether, alkylcarbonyloxy, nitro, phosphoro.

6. The process of claim 4 wherein R is methyl.

7. The process of claim 3 wherin the temperature is from about 30° C. to 80° C. and the ozone-containing gas has an ozone concentration of from about 0.5 to 4.0% by weight and the contact time is from about 10 minutes to 4 hours.

8. The process of claim 1 wherein the alkanesulfonic acid is dissolved in water or an inert organic solvent to provide an acid concentration by weight of from about 10% to saturation.

9. The process of claim 1 wherein the alkanesulfonic acid is treated as a neat liquid.

* * * * *